US006692475B2

(12) United States Patent
Mishima

(10) Patent No.: US 6,692,475 B2
(45) Date of Patent: Feb. 17, 2004

(54) DISPOSABLE DIAPER WITH SKIN-CONTACTABLE SHEETS SPACED ABOVE SKIN-CONTACTABLE SURFACE

(75) Inventor: Yoshitaka Mishima, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 104 days.

(21) Appl. No.: 10/016,051

(22) Filed: Dec. 6, 2001

(65) Prior Publication Data

US 2002/0068920 A1 Jun. 6, 2002

(30) Foreign Application Priority Data

Dec. 6, 2000 (JP) ........................................ 2000-371922

(51) Int. Cl.⁷ ............................................... A61F 13/15
(52) U.S. Cl. ............................... 604/385.19; 604/385.28
(58) Field of Search ....................... 604/385.01, 385.16, 604/385.22, 385.08, 385.19, 385.24, 385.28

(56) References Cited

U.S. PATENT DOCUMENTS

| | | | | |
|---|---|---|---|---|
| 5,599,338 A | * | 2/1997 | Enloe | 604/385.28 |
| 5,601,544 A | * | 2/1997 | Glaug et al. | 604/385.28 |
| 5,707,364 A | * | 1/1998 | Coates | 604/391 |
| 5,947,947 A | | 9/1999 | Tanzer et al. | |
| 6,017,336 A | | 1/2000 | Sauer | |
| 6,110,158 A | * | 8/2000 | Kielpikowski | 604/385.28 |
| 6,120,488 A | * | 9/2000 | VanRijswijck et al. | 604/385.28 |
| 6,458,114 B1 | * | 10/2002 | Mishima et al. | 604/385.24 |
| 6,497,693 B1 | * | 12/2002 | Otsubo | 604/385.19 |

FOREIGN PATENT DOCUMENTS

| | | |
|---|---|---|
| EP | 0 346 477 | 12/1989 |
| EP | 0 382 022 | 8/1990 |
| EP | 0 955 028 | 11/1999 |
| JP | 4-15921 | 2/1992 |

OTHER PUBLICATIONS

Copy of European Search Report dated Apr. 23, 2002.

* cited by examiner

Primary Examiner—Weilun Lo
Assistant Examiner—Michael G. Bogart
(74) Attorney, Agent, or Firm—Butzel Long

(57) ABSTRACT

A disposable undergarment that includes liquid-impervious skin-contactable sheets actually having a pair of belt-like strips spaced apart from and opposed to each other in a transverse direction of an undergarment and extending in a longitudinal direction of the undergarment along transversely opposite side edge portions of the undergarment. The skin-contactable sheets are attached to a skin-contactable surface 1a of the undergarment so as to cover a panel. The skin-contactable sheets have fixed surface areas secured to longitudinally opposite end portions 1c of the undergarment and free surface areas adapted to be spaced upward from the panel so that the skin-contactable surface may be partially surfaced between these skin-contactable sheets.

2 Claims, 8 Drawing Sheets

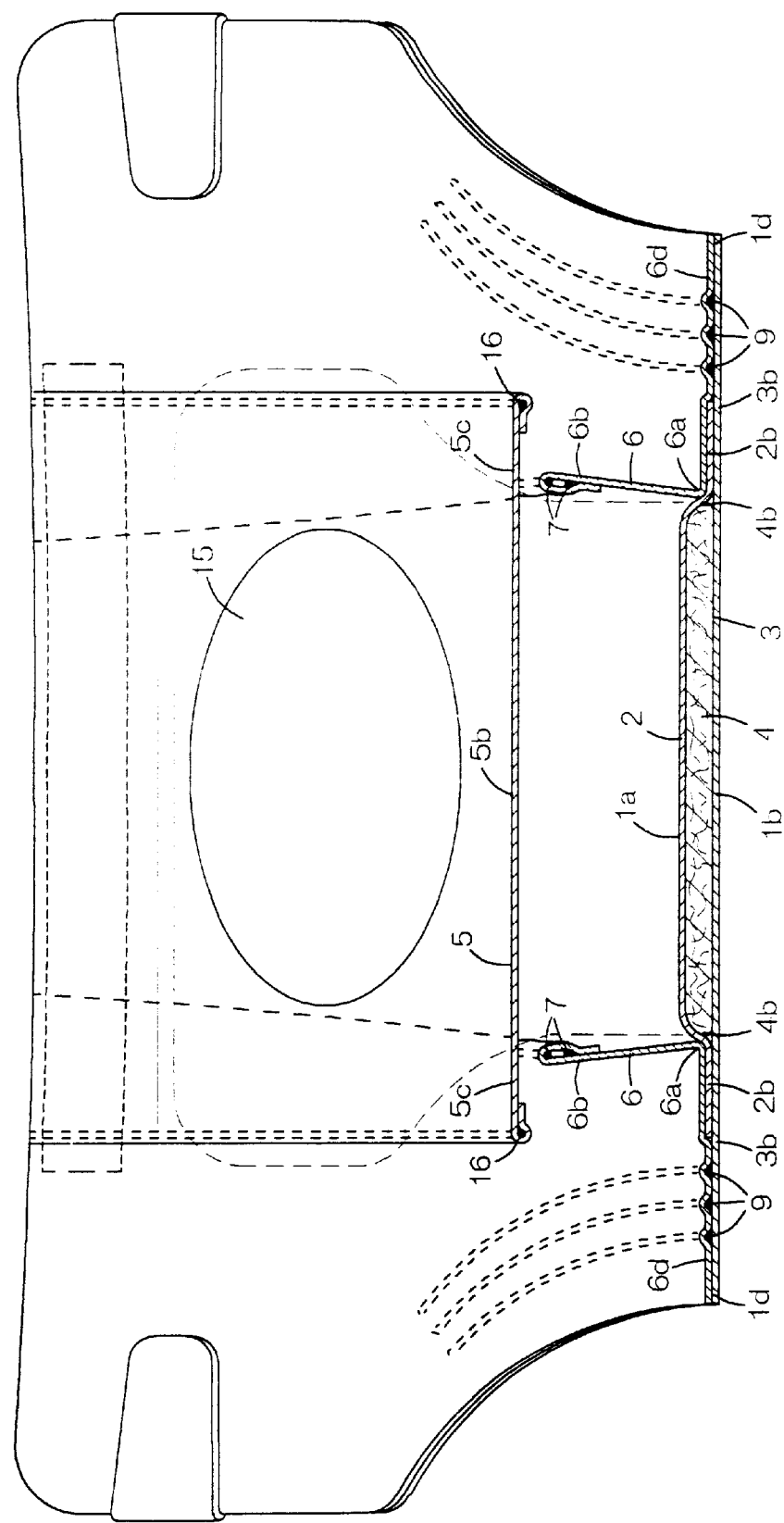

DISPOSABLE DIAPER WITH SKIN-CONTACTABLE SHEETS SPACED ABOVE SKIN-CONTACTABLE SURFACE

BACKGROUND OF THE INVENTION

This invention relates to a disposable undergarment adapted to absorb body excretion and then to hold it.

Japanese Utility Model Application Publication No. 1992-15921A discloses a disposable diaper comprising a liquid-pervious topsheet, a liquid-impervious base sheet, a liquid-absorbent panel disposed between these two sheets, and a non-stretchable apertured sheet having a plurality of pores wherein each of the apertures has an opening area of about 2 mm²-about 100 mm². This diaper is partially depressed in its thickness direction to define a pocket for feces. The porous sheet has its length as measured in a longitudinal direction shorter than that of the diaper and longitudinally opposite end portions of this apertured sheet are bonded to longitudinally opposite end portions of the diaper so as to cover the topsheet. The longitudinally opposite end portions lie above a level of the topsheet so that a longitudinally middle region of the apertured sheet is spaced upward from the topsheet and thereby defines a space between the topsheet and the apertured sheet.

With this diaper of prior art, loose feces is guided through the apertures of the apertured sheet into the pocket and only a small amount of loose feces held on the apertured sheet may cling to the wearer's skin. In this way, eruption of the wearer's skin due to loose feces clinging thereto can be minimized.

The apertured sheet has a plurality of apertures each dimensioned to pass body excretion such as urine or loose feces and therefore such excretion still held on the topsheet may flow back as the apertured sheet and the topsheet come in contact with each other. With this diaper of prior art, the apertured sheet is not elastically stretchable in the longitudinal direction of the diaper. In other words, the apertured sheet has no elastic force under which the longitudinally middle region of the apertured sheet is spaced upward from the topsheet as the diaper curves in the longitudinal direction with the topsheet inside and thereby this middle region comes in close contact with the wearer's crotch region. With this known diaper put on the wearer's body, the apertured sheet is slackened and its longitudinally middle region comes in contact with the topsheet. Consequently, the amount of body excretion flowing back through the apertured sheet may cling to the wearer's skin.

SUMMARY OF THE INVENTION

It is an object of this invention to provide a disposable undergarment provided with skin-contactable sheets adapted to be placed very stably against the wearer's crotch region as the undergarment is put on the wearer's body and thereby to prevent an amount of urine or loose feces still held on a skin-contactable surface of the undergarment from clinging to the wearer's skin.

According to this invention, there is provided a disposable undergarment comprising a liquid-impervious base sheet contoured by longitudinally opposite end portions extending in a transverse direction and transversely opposite side edge portions extending in a longitudinal direction, and a liquid-absorbent panel attached to the base sheet wherein the article has a skin-contactable surface on which the panel lies and a non skin-contactable surface opposed to the skin-contactable surface.

The skin-contactable sheets being stretchable in the longitudinal direction and substantially liquid-impervious are attached under extension in the longitudinal direction to the skin-contactable surface of the undergarment so as to cover the panel, the skin-contactable sheets having fixed surface areas secured to the longitudinally opposite end portions, respectively, and free surface areas extending between respective pairs of the fixed surface areas and not fixed to the undergarment so as to be spaced upward from the panel as the article curves in the longitudinal direction with its skin-contactable surface inside, wherein the skin-contactable surface of the article is provided with regions in which the skin-contactable sheets are absent so that the skin-contacting surface inclusive of the panel is partially surface in the regions.

According to one embodiment of this invention, the skin-contactable sheets actually comprise a pair of belt-like strips spaced from and opposed to each other in the transverse direction and respectively extending along the transversely opposite side edge portions of the undergarment in the longitudinal direction so that the skin-contactable surface inclusive of the panel may be partially surfaced between these skin-contactable sheets.

According to another embodiment of this invention, the undergarment further comprises a pair of substantially liquid-impervious leak-barrier cuffs spaced apart from and opposed to each other in the transverse direction and respectively extending along the transversely opposite side edge portions of the undergarment, the leak-barrier cuffs being disposed between the base sheet and the skin-contactable sheets and attached under extension in the longitudinal direction to the skin-contacting surface of the undergarment, the leak-barrier cuffs having fixed side edge portions secured to the transversely opposite side edge portions of the undergarment and extending in the longitudinal direction, free side edge portions being stretchable in the longitudinal direction and normally biased to rise on the skin-contactable surface and longitudinally opposite fixed end portions collapsed onto the skin-contactable surface and fixed to the longitudinally opposite end portions of the undergarment in such collapsed state so that the free surface area of the skin-contactable sheet is kept spaced upward from the free side edge portions of the leak-barrier cuffs.

According to still another embodiment of this invention, the skin-contactable sheet is made of an elastically stretchable fibrous nonwoven fabric.

According to further another embodiment of this invention, the skin-contactable sheet is made of a non-stretchable fibrous nonwoven fabric and elastically stretchable members are attached under extension in the longitudinal direction to the non-stretchable fibrous fabric so that the skin-contactable sheet may have stretchability in the longitudinal direction.

BRIEF DESCRIPTION OF THE DRAWINGS

FIG. 8 is a sectional view of the diaper taken along a line D—D in FIG. 5.

DETAILED DESCRIPTION OF THE INVENTION

Details of a disposable undergarment according to this invention will be more fully understood from the description of an open-type diaper given hereunder with reference to the accompanying drawings as a typical embodiment of this invention.

Figure 1:
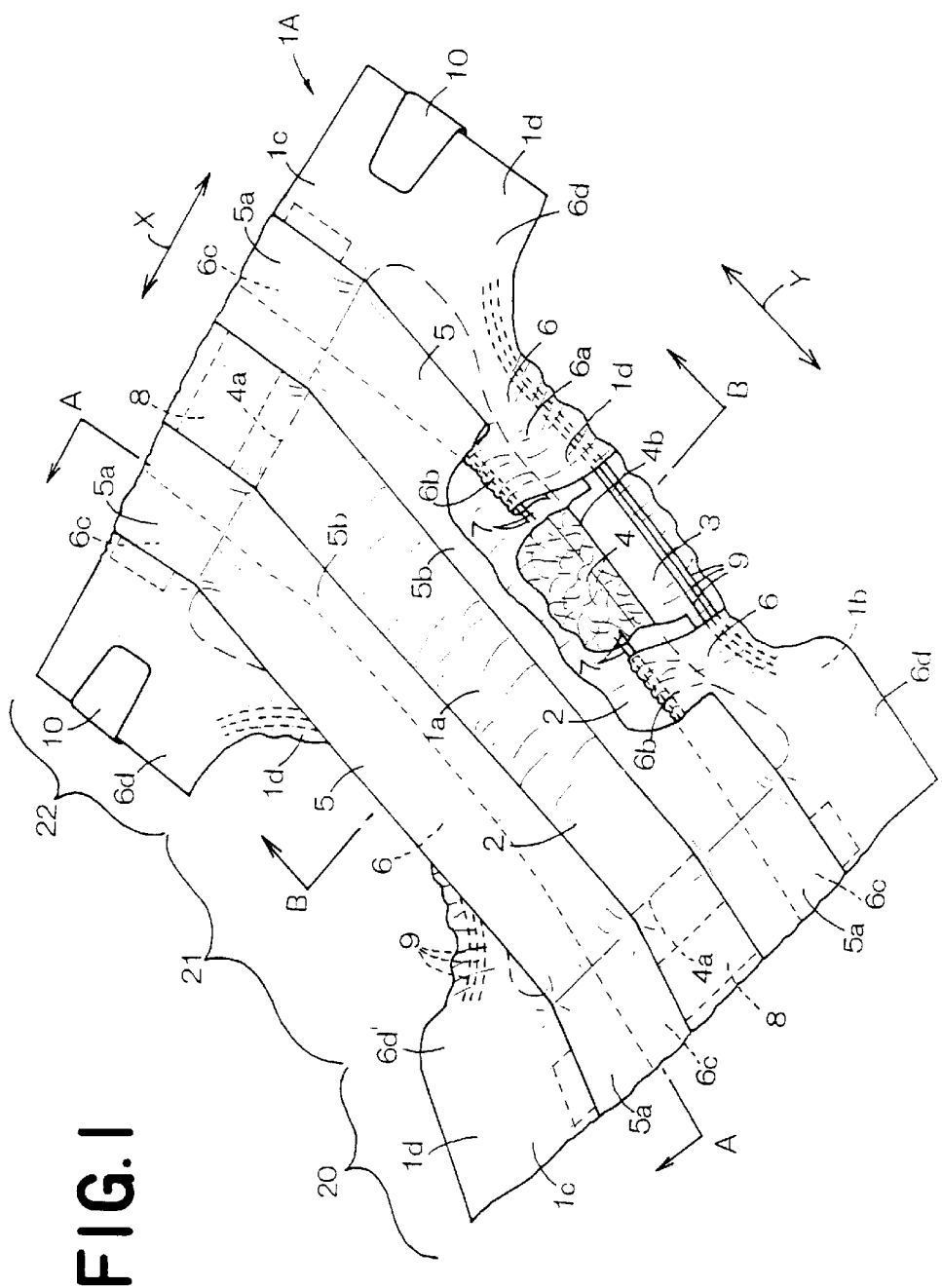
FIG. 1 is a perspective view of a diaper viewed from skin-contacting surface thereof as partially broken away.
Figure 2:
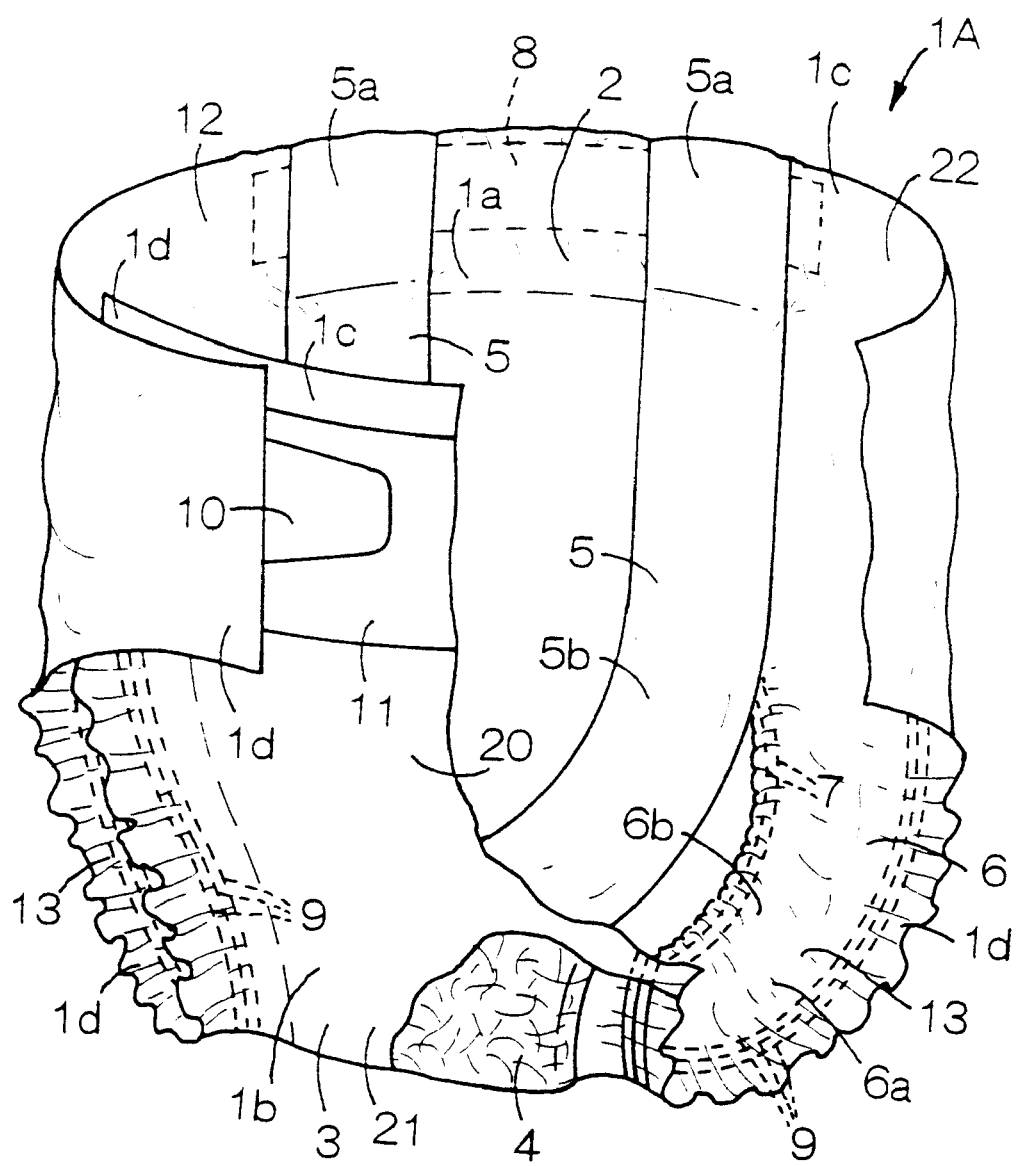
FIG. 2 is a partially cutaway perspective view of the diaper in a state worn with front and rear waist regions thereof connected to each other.
Figure 3:
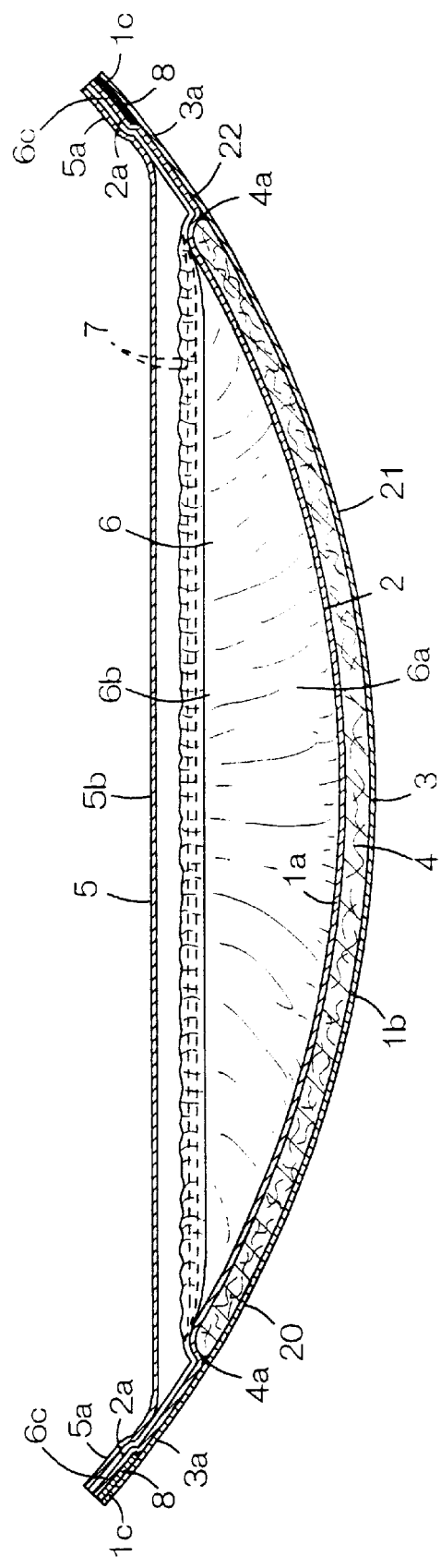
FIG. 3 is a sectional view of the diaper taken along a line A—A in FIG. 1.
Figure 4:
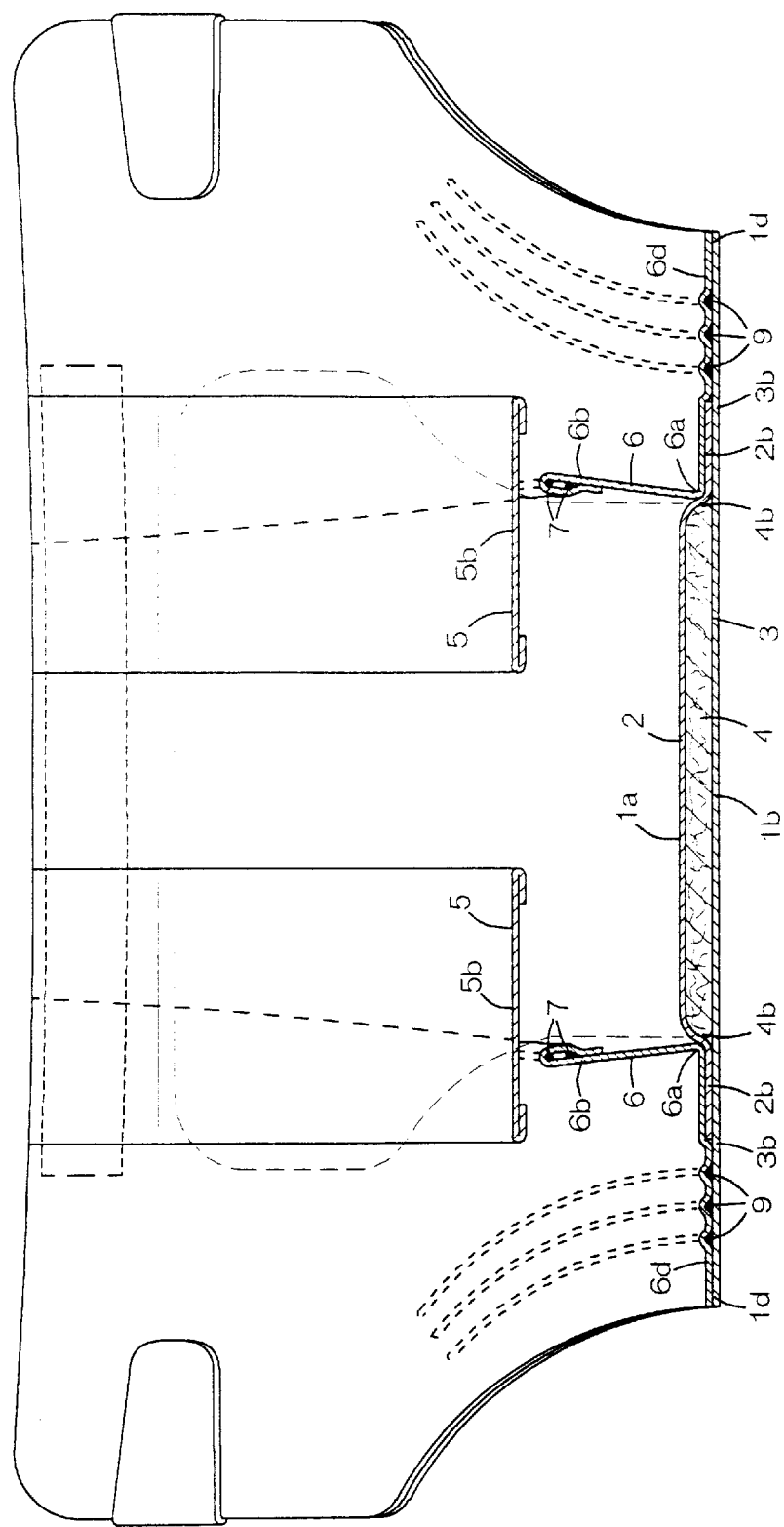
FIG. 4 is a sectional view of the diaper taken along a line B—B in FIG. 1.

FIG. 1 is a partially cutaway perspective view of the diaper 1A viewed from the side of a skin-contactable surface 1a thereof, FIG. 2 is a partially cutaway perspective view of the diaper 1A in a state of being worn with front and rear waist regions 20, 22 thereof connected to each other, FIG. 3 is a sectional view taken along a line A—A in FIG. 1 and FIG. 4 is a sectional view of the diaper taken along a line B—B in FIG. 1. In FIG. 1, a longitudinal direction is indicated by an arrow Y and a transverse direction is indicated by an arrow X. The surface referred to herein as the skin-contactable surface 1a should be understood to be the surface of the diaper 1A intended to be opposed to the wearer's skin and the surface of the diaper 1A referred to herein as a non skin-contactable surface 1b should be understood to be the surface of the diaper 1A intended to be not opposed to the wearer's skin when the diaper 1A is put on the wearer's body.

The diaper 1A comprises a liquid-pervious topsheet 2, a liquid-impervious base sheet 3 and a liquid-absorbent panel 4 disposed between these topsheet 2 and base sheet 3, and this panel 4 is entirely covered with and bonded to tissue paper (not shown). The panel 4 is bonded to the topsheet 2 as well as to the base sheet 3 with the tissue paper lying therebetween. In addition to these sheets 2, 3 and panel 4, the diaper 1A comprises substantially liquid-impervious skin-contacting sheets 5 and substantially liquid-impervious leak-barrier cuffs 6.

The diaper 1A is composed, in the longitudinal direction, of a front waist region 20, a rear waist region 22 and a crotch region 21 extending between these front and rear waist regions 20, 22, and has longitudinally opposite end portions 1c and transversely opposite side edge portions 1d. In the crotch region 21, the transversely opposite side edge portions id are curved inward by in the transverse direction like an ark. Of the diaper 1A, the topsheet 2 defines the skin-contactable surface 1a and the base sheet 3 defines the non skin-contacting surface 1b.

The skin-contactable sheets 5 actually comprise a pair of belt-like strips spaced apart from and opposed to each other in the transverse direction and extending along the respective side edge portions id in the longitudinal direction. These skin-contacting sheets 5 are made of a fibrous nonwoven fabric having elastic stretchability in the longitudinal direction as well as in the transverse direction. The skin-contactable sheets 5 are attached under extension in the longitudinal direction to the skin-contactable surface 1a. The skin-contactable sheets 5 respectively have fixed surface areas 5a secured to the longitudinally opposite end portions 1c and free surface areas 5b extending between the fixed surface areas 5a and not fixed to the diaper 1A so that the respective free surface areas 5b intermittently cover the vicinity of transversely opposite side edges 4b of the panel 4 with the topsheet 2 lying therebetween.

The tensile force of the respective skin-contactable sheets 5 enables the free surface areas 5b thereof to be separated upward from the panel 4 as the diaper 1A curves in the longitudinal direction with the topsheet 2 inside. Between these skin-contactable sheets 5, the topsheet 2 is partially surfaced.

The leak-barrier cuffs 6 are disposed between the topsheet 2 and the skin-contactable sheets 5 so as to be spaced apart from and opposed to each other in the transverse direction and to extend along the respective side edge portions 1d in the longitudinal direction. The leak-barrier cuffs 6 respectively comprise fixed side edge portions 6a secured to the respective side edge portions 1d, free side edge portions 6b adapted to rise on the topsheet 2 and fixed longitudinally opposite end portions 6c collapsed inward in the transverse direction of the diaper 1A and fixed to the associated longitudinally opposite end portions 1c in such collapsed state. The leak-barrier cuffs 6 further comprise outermost lateral portions 6d extending outward from the respective fixed side edge portions 6a in the transverse direction.

The fixed side edge portions 6a extend in the longitudinal direction immediately outside the transversely opposite side edges 4b of the panel 4. The free side edge portions 6b extend in the longitudinal direction in parallel to the respective fixed side edge portions 6a. The free side edge portions 6b are respectively provided with elastic members 7 bonded under extension thereto. These elastic members 7 associated with the respective cuffs are covered with parts of the respective free side edge portions 6b.

The longitudinally opposite end portions 1c of the diaper 1A are respectively provided with ribbon-like elastic members 8 extending in the transverse direction bonded under extension thereto. The transversely opposite side edge portions 1d are respectively provided with a plurality of elastic members 9 extending in the longitudinal direction bonded under extension thereto.

In the rear waist region 22, the transversely opposite side edge portions 1d are respectively provided with tape fasteners 10 extending inward in the transverse direction. The tape fasteners 10 respectively have proximal end portions disposed between the base sheet 3 and the outermost lateral portions 6d of the associated leak-barrier cuffs 6 and bonded to them. The tape fasteners 10 respectively have free end portions coated with pressure-sensitive adhesive (not shown). In the front waist region 20, the non skin-contactable surfaces 1b is provided with a rectangular target tape strip 11 (See FIG. 2) made of a plastic film. The target tape strip 11 serves as a fastening zone for the tape fasteners 10.

To wear the diaper 1A, the transversely opposite side edge portions 1d in the rear waist region 22 may be placed upon the outer side of the transversely opposite side edge portions 1d in the front waist region 20, then the free end portions of the respective tape fasteners 10 may be anchored on the target tape strip 11 by means of the pressure-sensitive adhesive to connect the front waist region 20 with the rear waist region 22.

A waist-opening 12 and a pair of leg-openings 13 are defined in the diaper 1A, as seen in FIG. 2, as the front and rear waist regions 20, 22 are connected to each other in the manner as described above. The diaper 1A curves in the longitudinal direction with the topsheet 2 inside whereupon contract of the elastic members 7 associated with the respective leak-barrier cuffs 6 causes the free side edge portions 6b of the respective cuffs 6 to rise on the topsheet 2 and the tension of the skin-contactable sheets 5 causes the free surface areas 5b thereof to be spaced above the free side edge portions 6b of the leak-barrier cuffs 6.

With the diaper 1A put on the wearer's body, the free surface areas 5b of the respective skin-contactable sheets 5 spaced above the free side edge portions 6b of the respective cuffs 6 are reliably maintained in close contact with the wearer's crotch region. Specifically, it is not likely that the skin-contactable sheets 5 might slide away from the wearer's crotch region even if the diaper 1A moves from its initial position to some degree due to movement of the wearer. The skin-contactable sheets 5 disposed between the wearer's skin and the topsheet 2 advantageously prevent urine or loose feces held on the topsheet 2 from clinging to the wearer's skin.

The skin-contactable sheets 5 are made of a liquid-impervious fibrous nonwoven fabric and therefore are capable of preventing any quantity of urine or loose feces held on the topsheet 2 from permeating these skin-contactable sheets 5 and clinging to the wearer's skin even if the skin-contactable sheets 5 come in contact with the topsheet 2.

With this diaper 1A, the free side edge portions 6b of the leak-barrier cuffs 6 rising on the topsheet 2 form barriers against excretion such as urine or loose feces which may spread over the topsheet 2 and reach the transversely opposite side edge portions 1d of the diaper 1A and these barriers reliably prevent such excretion from leaking beyond the respective side edge portions 1d.

With the diaper 1A put on the wearer's body, the free surface areas 5b of the skin-contactable sheets 5 are kept to be spaced above the free side edge portions 6b of the respective leak-barrier cuffs 6 and therefore there is no anxiety that the free surface areas 5b might collapse the free side edge portion from above and thereby impair the desired function of the free side edge portions 6b as the barriers.

Along the longitudinally opposite end portions 1c of the diaper 1A, as best seen in FIG. 3, the longitudinally opposite end portions 2a of the topsheet 2 and the longitudinally opposite end portions 3a of the base sheet 3 extend outward beyond the longitudinally opposite edges 4a of the core 4 in the longitudinal direction so that these end portions 2a, 3a are overlaid with each other and bonded together. The fixed end portions 6c of the respective leak-barrier cuffs 6 are bonded to the end portions 2a of the topsheet 2. The fixed surface areas 5a of the respective skin-contactable sheets 5 are bonded to the end portions 2a of the topsheet 2 as well as to the fixed end portions 6c of the respective leak-barrier cuffs 6. The elastic members 8 associated with the waist-opening are disposed between and bonded to the respective end portions 2a and end portions 3a.

Along the transversely opposite side edge portions 1d of the diaper 1A, as best seen in FIG. 4, the transversely opposite side edge portions 2b of the topsheet 2 extend outward slightly beyond transversely opposite side edges 4b of the core 4 in the transverse direction and the transversely opposite side edge portions 3b of the base sheet 3 as well as the outermost lateral portions 6d of the leak-barrier cuffs 6 extend further outward beyond the side edge portions 2b of the topsheet 2 in the transverse direction. The side edge portions 2b of the topsheet 2 are disposed between and bonded to the side edge portions 3b and the outermost lateral portions 6d, respectively. The side edge portions 3b and the outermost lateral portions 6d are overlaid with each other and bonded together. The fixed side edge portions 6a of the respective leak-barrier cuffs 6 are bonded to the respective side edge portions 2b of the topsheet 2. The elastic members 9 associated with the leg-openings are disposed between and bonded to the side edge portions 3b of the base sheet 3 and the outermost lateral portions 6d of the leak-barrier cuffs 6, respectively.

Figure 5:
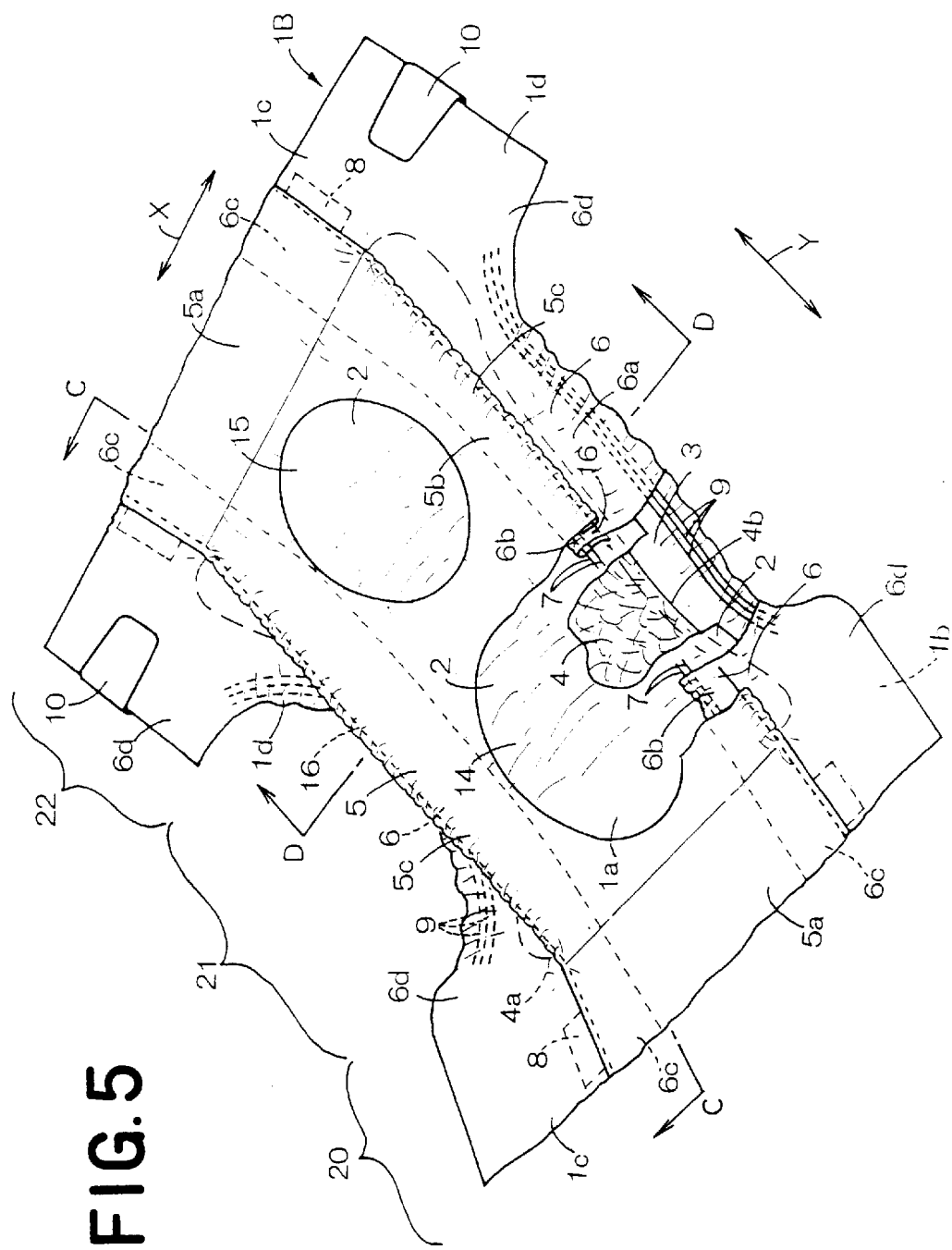
FIG. 5 is a partially cutaway perspective view of another embodiment of the diaper.
Figure 6:
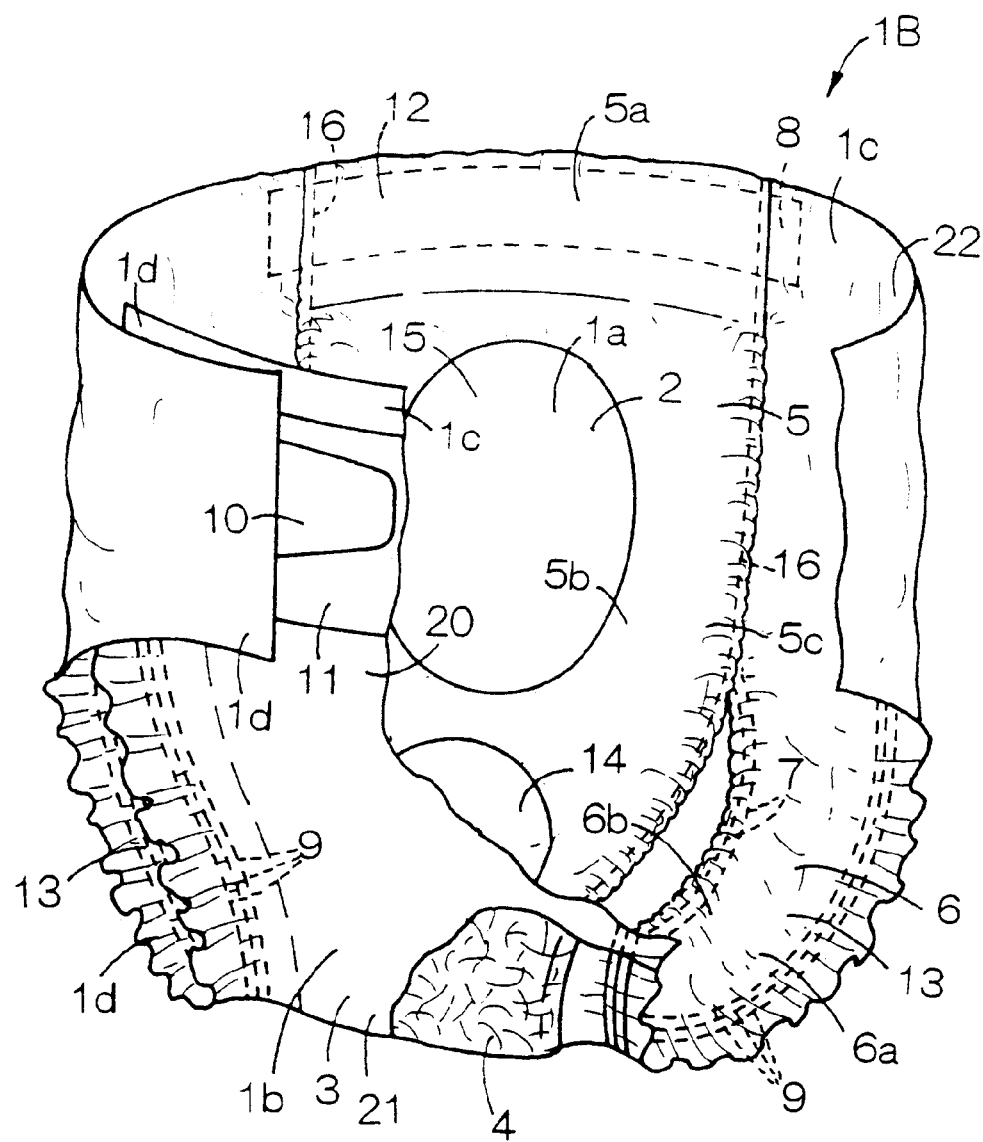
FIG. 6 is a partially cutaway perspective view of another embodiment of the diaper in a state of being worn with front and rear waist regions thereof connected to each other.
Figure 7:
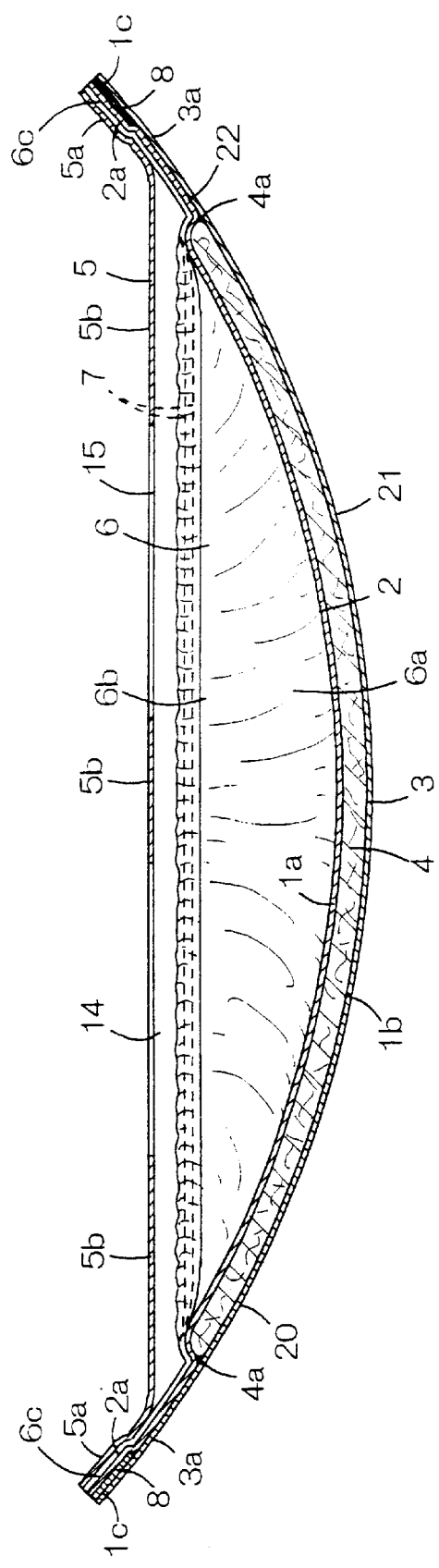
FIG. 7 is a sectional view of the diaper taken along a line C—C in FIG. 5.

FIG. 5 is a partially cutaway perspective view showing a diaper 1B according to another embodiment of this invention, FIG. 6 is a partially cutaway perspective view showing this diaper 1B as put on the wearer's body with the front and rear waist regions 20, 22 connected to each other and, FIG. 7 is a sectional view taken along a line A—A in FIG. 5 and FIG. 8 is a sectional view taken along a line B—B in FIG. 5. In FIG. 5, the longitudinal direction is indicated by an arrow Y and the transverse direction is indicated by an arrow X. The diaper 1B shown in FIG. 5 is distinguished from the diaper 1A shown in FIG. 1 in arrangement as will be described.

In the case of this diaper 1B, the skin-contacting sheet 5 is formed by a non-stretchable fibrous nonwoven fabric presenting a substantially rectangular shape which is larger in the longitudinal direction. The skin-contactable sheet 5 is provided along transversely opposite side edge portions 5c thereof with longitudinally extending elastic members 16 bonded under extension thereto, respectively, so that the skin-contactable sheet 5 may be stretchable in the longitudinal direction. The elastic members 16 are covered with parts of the respective side edge portions 5c.

The skin-contactable sheet 5 is attached under extension in the longitudinal direction to the skin-contactable surface 1a of the diaper 1B. The skin-contactable sheet 5 has the fixed surface areas 5a secured to the longitudinally opposite end portions 1c of the diaper 1B and the free surface area 5b extending between the fixed surface areas 5a and not fixed to the diaper 1B so that the free surface area 5b indirectly cover the panel 4 substantially over its entire area with the topsheet 2 lying therebetween.

The free surface area 5b of the skin-contactable sheet 5 defines an opening 14 in the front waist region 20 and an opening 15 in the rear waist region 22. The topsheet 2 is partially surfaced in these openings 14, 15.

In the similar manner to the case shown by FIG. 1, the tensile force of the skin-contactable sheet 5 enables its free surface area 5b to be separated upward from the panel 4 as the diaper 1B curves in the longitudinal direction with the topsheet 2 inside.

With the diaper 1B put on the wearer's body, the free side edge portions 6b of the respective leak-barrier cuffs 6 rise on the topsheet 2 as the elastic members 7 associated therewith contract and the free surface area 5b of the skin-contactable sheet 5 is spaced upward from the free side edge portions 6b of the leak-barrier cuffs 6, as will be apparent from FIG. 6. More specifically, the openings 14, 15 of the skin-contactable sheet 5 correspond to the positions of the urinary organs and the anus of the wearer, respectively, as the diaper 1B is worn.

With this diaper 1B worn, the skin-contactable sheet 5 is maintained in close contact with the wearer's crotch region more stably than in the case of the paired skin-contactable sheets 5 and the preventive effect against the anxiety that the amount of urine or loose feces held on the topsheet 2 might cling to the wearer's skin can be correspondingly improved. In this diaper 1B also, the free side edge portions 6b of the respective leak-barrier cuffs 6 rising on the topsheet 2 advantageously function as the barriers as in the case of FIG. 1 and therefore there is not likely that urine or loose feces might leak beyond the transversely opposite side edge portions 1d of the diaper 1B.

The skin-contactable sheets 5 in FIG. 1 may be formed an elastically stretchable hydrophobic fibrous nonwoven fabric obtained by the melt blown or spun bond process. Component fiber of such elastic stretchable nonwoven fabric may be stretchable fibers may be stretchable fibers obtained by melting and spinning thermoplastic elastomer resin. The elastically stretchable fibrous nonwoven fabric may be a composite nonwoven fabric consisting of a hydrophobic fibrous nonwoven fabric made of thermoplastic elastomer resin fiber and a hydrophobic fibrous nonwoven fabric comprising crimped fiber which is obtained by melting and spinning thermoplastic synthetic resin such as polypropylene, polyethylene or polyester bonded to at least one surface of the hydrophobic fibrous nonwoven fabric.

The topsheet 2 may be formed of a hydrophilic fibrous nonwoven fabric or finely porous plastic film. The base sheet 3 may be formed of a hydrophobic fibrous nonwoven fabric, a liquid-impervious plastic film, a two-layered hydrophobic nonwoven fabric, or a composite sheet consisting of hydrophobic fibrous nonwoven fabric laminated with a plastic film. The skin-contacting sheet 5 as well as the leak-barrier cuffs 6 in FIG. 6 may be formed of a hydrophobic fibrous nonwoven fabric.

It is also possible to form the base sheet 3 as well as the skin-contactable sheet 5 and the leak-barrier cuffs 6 as shown in FIG. 6 using a composite nonwoven fabric comprising a melt blown fibrous nonwoven fabric with a high water-resistance property sandwiched between two layers of spun bond fibrous nonwoven fabric having high strength and flexibility.

The nonwoven fabric used as stock material for the topsheet 2 and the base sheet 3 as well as for the skin-contactable sheet 5 and the leak-barrier cuffs 6 as shown in FIG. 6 may be selected from a group consisting of those obtained by spun lacing, needle punching, melt blowing, thermal bonding, spun bonding, chemical bonding and air-through processes. The component fiber of such nonwoven fabric may be selected from a group consisting of polyolefine-, polyester- and polyamide-fiber, and core-sheath type conjugated fiber or side-by-side type conjugated fiber of polyethylene/polypropylene or polyethylene/polyester.

The core 4 comprises a mixture of fluff pulp and super-absorptive polymer particles or a mixture of fluff pulp, superabsorptive polymer particles and thermoplastic synthetic resin fiber compressed to a desired thickness. The superabsorptive polymer may be selected from a group consisting of starch-based polymer, cellulose-based polymer and synthetic polymer.

Both in the diaper 1A and the diaper 1B, the presence of the topsheet 2 is not essential so far as the base sheet 3 is provided with the liquid-absorbent panel 4 attached thereto. In this case, the panel 4 preferably comprises fibrous web with appropriate compressive restoring elasticity, which contains the superabsorptive polymer particles dispersed and held in fiber-interstices thereof and which has been compressed to a desired thickness to give a shape stability. The component fiber of such fibrous web may be selected from a group consisting of polyolefine-based fiber such as polypropylene or polyethylene, polyester-based fiber such as polyethylene terephthalate, polyamide-based fiber such as nylon 66 or nylon 6, acryl-based fiber, and cellulose-based fiber such as pulp, rayon or acetate.

Bonding between the topsheet 2 and the base sheet 3, fixing of the skin-contactable sheets 5 and the leak-barrier cuffs 6, joining of the core 4, and attachment of the respective elastic members 7, 8, 9, 16 may be achieved using hot melt adhesive or heat welding technique such as heat-sealing or sonic-sealing.

This invention is applicable not only to the open-type diaper but also to a pants-type diaper having its front and rear waist regions previously connected to each other.

With the disposable undergarment according to this invention, the free surface areas of the respective skin-contactable sheets are spaced upward from the liquid-absorbent panel by tensile force of the skin-contactable sheets as the undergarment longitudinally curved with its skin-contactable surface inside. With the undergarment put on the wearer's body, the free surface areas of the respective skin-contactable sheets are kept in sufficiently close contact with the wearer's crotch region to prevent the skin-contactable sheets from getting out of the wearer's crotch region even if the undergarment moves away due to movement of the wearer's body. The skin-contactable sheets disposed between the wearer's skin and the skin-contactable surface of the undergarment are substantially liquid-impervious, so there is no anxiety that any amount of urine or loose feces still held on the skin-contactable surface might cling to the wearer's skin. Should the skin-contactable sheets come in contact with the skin-contactable surface, there is no fear that such excretion still held on the skin-contactable surface might permeate the skin-contactable sheets and cling to the wearer's skin.

According to the embodiment in which the leak-barrier cuffs respectively extend along the transversely opposite side edge portions of the article in the longitudinal direction, contraction of the elastic members associated with these leak-barrier cuffs causes the free side edge portions of these leak-barrier cuffs to rise on the skin-contactable surface as the article is put on the wearer's body. The free side edge portions rising in this manner form the barriers against urine or loose feces so that such excretion is reliably prevented thereby from leaking beyond the transversely opposite side edge portions of the article even when such excretion spreads on the skin-contacting surface and then reaches the side edge portions of the undergarment. In the undergarment provided with the leak-barrier cuffs, the free surface areas of the respective skin-contactable sheets remain spaced upward from the free side edge portions of the respective leak-barrier cuffs so that the free side edge portions can reliably function as the barriers without being collapsed downward by the free surface area.

What is claimed is:
1. A disposable undergarment comprising:
   a skin-contactable surface;
   a non skin-contactable surface opposed to the skin-contactable surface;
   a liquid-impervious base sheet;
   longitudinally opposed end portions extending in a transverse direction and transversely opposite side edge portions extending in a longitudinal direction;
   a liquid-absorbent panel positioned between said skin-contactable surface and said non skin-contacting surface;
   a pair of skin-contactable sheets which are stretchable in said longitudinal direction and substantially liquid-impervious, said skin-contactable sheets having fixed surface areas and free surface areas between said fixed surface areas, said pair of skin-contactable sheets being attached under extension in said longitudinal direction at said fixed surface areas to said skin-contactable surface with said pair of skin-contactable sheets spaced apart from and opposed to each other in said transverse direction and extending along said transversely opposite side edge portions so that said free surface areas are spaced apart upward from said liquid-absorbent panel as said undergarment curves in said longitudinal direction with its skin-contactable surface inside; and a pair of substantially liquid-impervious leak-barrier cuffs spaced apart from and opposed to each other in said transverse direction and extending along said transversely opposite side edge portions of said undergarment, said pair of leak-barrier cuffs being disposed between said base sheet and said skin-contactable sheets and attached in said longitudinal direction to said skin-contactable surface, said leak-barrier cuffs having fixed side edge portions fixed to said transversely opposite side edge portions of said undergarment and extending in said longitudinal direction, free side edge portions being stretchable in said longitudinal direction and normally biased to rise on said skin-contactable surface and longitudinally opposite fixed end portions collapsed onto said skin-contactable surface and fixed to said longitudinally opposite end portions in a collapsed state so that said free surface areas of said skin-contactable sheets are kept spaced upward from said free side edge portions of said leak-barrier cuffs.

2. The disposable undergarment according to claim 1, wherein said skin-contactable sheets comprise an elastically stretchable fibrous nonwoven fabric.

* * * * *